(12) United States Patent
Funke et al.

(10) Patent No.: US 10,189,800 B2
(45) Date of Patent: Jan. 29, 2019

(54) METHOD FOR PREPARING N-(1,3,4-OXADIAZOL-2-YL) ARYLCARBOXAMIDES

(71) Applicant: Bayer CropScience Aktiengesellschaft, Monheim am Rhein (DE)

(72) Inventors: Christian Funke, Leichlingen (DE); Arnd Neeff, Burscheid (DE); Sergii Pazenok, Solingen (DE); Norbert Lui, Odenthal (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/763,181

(22) PCT Filed: Sep. 23, 2016

(86) PCT No.: PCT/EP2016/072629
§ 371 (c)(1),
(2) Date: Mar. 26, 2018

(87) PCT Pub. No.: WO2017/055175
PCT Pub. Date: Apr. 6, 2017

(65) Prior Publication Data
US 2018/0273496 A1  Sep. 27, 2018

(30) Foreign Application Priority Data
Sep. 28, 2015 (EP) .................................... 15187023

(51) Int. Cl.
*C07D 271/113* (2006.01)
(52) U.S. Cl.
CPC ......... *C07D 271/113* (2013.01); *Y02P 20/582* (2015.11)
(58) Field of Classification Search
CPC ................................................ C07D 271/113
See application file for complete search history.

(56) References Cited

FOREIGN PATENT DOCUMENTS

| WO | 02/26731 A2 | 4/2002 |
|---|---|---|
| WO | 2008/004117 A1 | 1/2008 |
| WO | 2012/028579 A1 | 3/2012 |
| WO | 2012/126932 A1 | 9/2012 |
| WO | 2012/130780 A1 | 10/2012 |
| WO | 2013/064459 A1 | 5/2013 |
| WO | 2013/124228 A1 | 8/2013 |
| WO | 2014/114779 A1 | 7/2014 |

OTHER PUBLICATIONS

Zhur. Org Khim., vol. 25, No. 10, p. 2216, 1989.
Goswami, S. et al, "Molecular Recognition: Hydrogen bonding induced configurational locking of a new Photoresponsive receptor by Dicarboxylic acids," Tetrahedron Letters, Pergamon, GB, vol. 40, No. 9, pp. 1735-1738, Feb. 26, 1999, XP004157179.
Jarrahpour, Aliasghar et al., "Synthesis of some new monocyclic [beta]-lactams as antimalarial agents," Iranian Chemical Society Journal, vol. 12, No. 12,pp. 2083-2092, Jun. 27, 2015, XP055235675.
International Search Report of International Patent Application No. PCT/EP2016/072629 dated Nov. 16, 2016.

*Primary Examiner* — Shawquia Jackson
(74) *Attorney, Agent, or Firm* — McBee Moore Woodward & Vanik IP, LLC

(57) ABSTRACT

A method for preparing N-(1,3,4-oxadiazol-2-yl)arylcarboxamides of formula (I) is described.

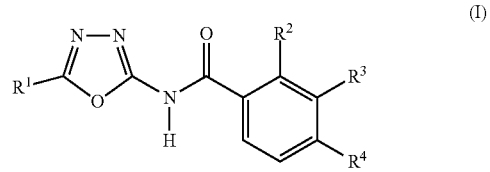

(I)

The substituents therein are radicals such as hydrogen, alkyl, haloalkyl or aryl.

11 Claims, No Drawings

METHOD FOR PREPARING N-(1,3,4-OXADIAZOL-2-YL) ARYLCARBOXAMIDES

CROSS REFERENCE TO RELATED APPLICATIONS

This application is a National Stage entry of International Application No. PCT/EP2016/072629 filed 23 Sep. 2016, which claims priority to European Patent Application No. 15187023.5, filed 28 Sep. 2015.

BACKGROUND

Field

The invention relates to a method for preparing herbicidally active N-(1,3,4-oxadiazol-2-yl)arylcarboxamides.

Description of Related Art

WO 2012/126932 A1 discloses herbicidally active N-(1,3,4-oxadiazol-2-yl)arylcarboxamides. A method for their preparation is also described therein. In this method, substituted benzoic acids are reacted with 2-amino-1,3,4-oxadiazoles, which are substituted in the 5-position, in the presence of activating reagents such as carbonylimidazole (CDI), dicyclohexylcarbodiimide or 2,4,6-tripropyl-1,3,5,2,4,6-trioxatriphosphorinane-2,4,6-trioxide. Such reagents however are unsuitable for reactions on a large scale since they are very expensive and cannot be reused. It is known from Zhur. Org Khim. V. 25, N. 10, 1989, 2216 that substituted benzoyl chlorides react with 2-amino-1,3,4-oxadiazole not only to give the desired 2-benzoylamino-1,3,4-oxadiazoles but also to give the isomeric 3-benzoyl-2-imino-1,3,4-oxadiazolines.

SUMMARY

It is an object of the present invention to provide a method for preparing N-(1,3,4-oxadiazol-2-yl)arylcarboxamides which overcomes the disadvantages of the methods known from the prior art.

It has now been found that N-(1,3,4-oxadiazol-2-yl)arylcarboxamides may be prepared cost-effectively and in high yields by reaction of substituted benzoic acids with 2-amino-1,3,4-oxadiazoles, substituted in the 5-position, in the presence of an inexpensive activating reagent and a base.

The present invention therefore relates to a method for preparing N-(1,3,4-oxadiazol-2-yl)arylcarboxamides of general formula (I) by reacting 2-amino-1,3,4-oxadiazoles of general formula (II) with benzoic acids of general formula (III),

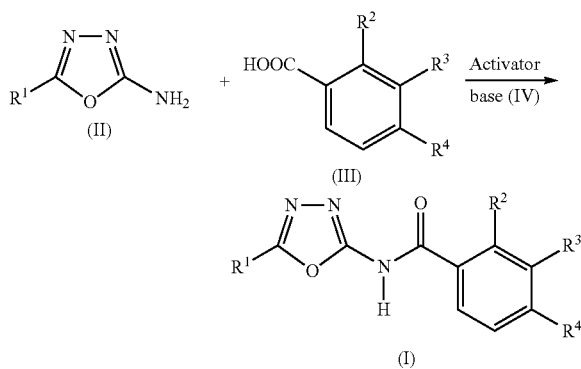

characterized in that said method is carried out
a) in the presence of an activating reagent (activator) from the group consisting of thionyl chloride, phosgene, diphosgene, mesyl chloride, tosyl chloride, $POCl_3$, $PCl_5$, oxalyl chloride and $C_1$-$C_8$-alkyl-OC(O)Cl, and
b) in the presence of a base of general formula (IV), $$(IV)$$

and
c) where the substituents are as defined hereinbelow:
$R^1$ is hydrogen, $C_3$-$C_{12}$-cycloalkyl, $C_1$-$C_8$-alkyl, $C_1$-$C_5$-alkoxy, halogen, cyano or phenyl,
$R^2$ is hydrogen, $C_1$-$C_5$-alkyl or halogen,
$R^3$ is hydrogen, $C_1$-$C_8$-alkyl, $C_1$-$C_8$-alkylsulphenyl, $C_1$-$C_8$-alkylsulphinyl or $C_1$-$C_8$-alkylsulphonyl,
$R^4$ is $C_1$-$C_5$-alkyl or $C_1$-$C_3$-haloalkyl,
$R^5$ is $C_1$-$C_{12}$-alkyl or phenyl.

DETAILED DESCRIPTION OF A PREFERRED EMBODIMENT

Key advantages of the method according to the invention are the high yield, the use of inexpensive reagents and the reusability of the base of formula (IV).

The substituted benzoic acids of formula (III) are known, for example, from WO 2012/126932 A1. 2-Amino-1,3,4-oxadiazoles of formula (II) are either commercially available or may be prepared from carboxylic hydrazides by the methods described, for example, in Tetrahedron, 69, 2013 2075-2080. The bases of formula (IV) are likewise commercially available or obtainable by methods known to those skilled in the art.

In the formulae (I), (II), (III) and (IV), alkyl radicals having more than two carbon atoms may be straight-chain or branched. Alkyl radicals are, for example, methyl, ethyl, n-propyl or isopropyl, n-, iso-, t- or 2-butyl, pentyls, hexyls such as n-hexyl, isohexyl and 1,3-dimethylbutyl. The same applies to alkoxy and cycloalkyl radicals.

Halogen is fluorine, chlorine, bromine or iodine, preferably fluorine or chlorine.

If a group is polysubstituted by radicals, this is to be understood as meaning that this group is substituted by one or more identical or different radicals selected from the radicals mentioned.

The compounds of the formulae (II) and (III) are typically used in a molar ratio of 0.8 to 1.5. The compound of formula (II) is preferably used with an excess of 10% relative to the compound of formula (III).

The activator and the compounds of the formula (III) are typically used in a molar ratio of 0.5 to 3, preferably of 1 to 2, particularly preferably of 1.2 to 1.9.

The activator used is preferably thionyl chloride, phosgene or diphosgene, particularly preferably thionyl chloride.

The base of the formula (IV) and the compounds of the formula (III) are typically used in a molar ratio of 0.5 to 10, preferably of 1 to 3, particularly preferably of 1 to 2.5.

The method according to the invention is generally carried out in a solvent. Suitable solvents are inert organic solvents, preferably aliphatic, alicyclic or aromatic hydrocarbons such as petroleum ether, hexane, heptane, cyclohexane, methylcyclohexane, benzene, toluene, xylene and decaline; halogenated hydrocarbons such as chlorobenzene, dichlorobenzene, dichloromethane, chloroform, tetrachloromethane, dichloroethane and trichloroethane; esters such as ethyl acetate and isopropyl acetate; ethers such as diethyl ether, diisopropyl ether, methyl tert-butyl ether, methyl tert-amyl ether, dioxane, tetrahydrofuran, 1,2-dimethoxyethane, 1,2-diethoxyethane and anisole; ketones such as acetone, butanone, methyl isobutyl ketone and cyclohexanone; nitriles such as acetonitrile, propionitrile, n- or isobutyronitrile and benzonitrile; amides such as N,N-dimethylformamide, N,N-dimethylacetamide, N-methylformanilide, N-methylpyrrolidone and hexamethylphosphoramide; pyridines such as 2-methylpyridine, 3-methylpyridine, 4-methylpyridine, 2,3-dimethylpyridine, 2-methyl-5-ethylpyridine, 2,6-dimethylpyridine, 2,4-dimethylpyridine, 3,4-dimethylpyridine and 2,4,6-trimethylpyridine. Mixtures of the abovementioned solvents are also suitable.

The solvent used in the method according to the invention is preferably tetrahydrofuran, acetonitrile, 3-methylpyridine or 2-methyl-5-ethylpyridine. Particular preference is given to 3-methylpyridine.

The method according to the invention is typically carried out in a temperature range of −5° to 50° C., preferably 0° to 25° C.

The method according to the invention is typically carried out such that the compounds of the formulae (II), (III) and (IV) are charged in a solvent and the activator is slowly added dropwise with stirring, or is introduced in the case of phosgene. The progress of the reaction can be monitored by HPLC. The reaction generally goes to completion after 10 to 20 hours.

After the reaction is complete, the reaction mixture is cooled and the product generally precipitates out virtually quantitatively. Alternatively, the reaction mixture can be diluted with a polar solvent such as water or alcohols such as isopropanol. The reaction product of the formula (I) is obtained in high purity and may, if required, be further purified. It is particularly advantageous to add water to the reaction mixture at a temperature between 20 and 35° C. over 3 to 6 hours. In this case the product is obtained in a rapidly filterable form. After treating the mother liquor with aqueous sodium hydroxide solution, about 95% of the base of the formula (IV) can be recovered by distillation.

The method according to the invention is preferably carried out with compounds of the formulae (II) and (III), where $R^1$ is hydrogen, methyl, ethyl, n-propyl, isopropyl or phenyl,
$R^2$ is methyl or chlorine,
$R^3$ is methylsulphenyl, methylsulphinyl or methylsulphonyl,
$R^4$ is trifluoromethyl,
$R^5$ is methyl or n-butyl.

The method according to the invention is particularly preferably carried out with compounds of the formulae (II) and (III), where $R^1$ is methyl,
$R^2$ is methyl or chlorine,
$R^3$ is methylsulphonyl,
$R^4$ is trifluoromethyl,
$R^5$ is methyl.

The preparation examples which follow more particularly elucidate the invention.

Preparation of 2-methyl-N-(5-methyl-1,3,4-oxadiazol-2-yl)-3-(methylsulphonyl)-4-(trifluoromethyl) benzamide, (Variant 1)

57 g (200 mmol) of 2-methyl-3-methylsulphonyl-4-trifluoromethylbenzoic acid, 21.8 g (220 mmol) of 2-amino-5-methyl-1,3,4-oxadiazole and 32.8 g (400 mmol) of N-methylimidazole were dissolved in 300 ml of 3-methylpyridine and stirred for 30 minutes. After cooling to 10° C., 38.2 g (320 mmol) of thionyl chloride were added dropwise over 60 minutes such that the temperature of the reaction mixture remained between 10° C. and 20° C. The reaction mixture was then stirred at 20° C. for another 18 hours. 200 ml of water were then added dropwise over 30 minutes such that the temperature of the reaction mixture remained between 25° C. and 30° C. The reaction mixture was stirred at 40 to 45° C. for 4 hours and was cooled to 20° C. After filtration, the product was washed with 200 ml of water and 100 ml of 5% hydrochloric acid. After drying the residue, 62.4 g of 2-methyl-N-(5-methyl-1,3,4-oxadiazol-2-yl)-3-(methylsulphonyl)-4-(trifluoromethyl)benzamide are obtained (yield 86%).

Preparation of 2-methyl-N-(5-methyl-1,3,4-oxadiazol-2-yl)-3-(methylsulphonyl)-4-(trifluoromethyl) benzamide, (Variant 2)

57 g (200 mmol) of 2-methyl-3-methylsulphonyl-4-trifluoromethylbenzoic acid, 21.8 g (220 mmol) of 2-amino-5-methyl-1,3,4-oxadiazole and 32.8 g (400 mmol) of N-methylimidazole were dissolved in 300 ml of 3-methylpyridine and stirred for 30 minutes. After cooling to 10° C., 38.2 g (320 mmol) of thionyl chloride were added dropwise over 60 minutes such that the temperature of the reaction mixture remained between 10° C. and 20° C. The reaction mixture was then stirred at 20° C. for another 18 hours. 200 ml of water were then added dropwise over 6 hours such that the temperature of the reaction mixture remained between 25° C. and 30° C. The resulting suspension was cooled to 15° C., filtered and the filter cake was washed with 200 ml of water and 100 ml of 5% hydrochloric acid. After drying the residue, 65.5 g of 2-methyl-N-(5-methyl-1,3,4-oxadiazol-2-yl)-3-(methylsulphonyl)-4-(trifluoromethyl)benzamide are obtained (yield 90%).

For comparative purposes, the reaction as described above was carried out, under otherwise the same conditions and stoichiometirc ratios, using the reagents known from WO 2012/126932 A1 of oxalyl chloride (instead of thionyl chloride) and 4-dimethylaminopyridine (instead of N-methylimidazole). This gave 11.1 g of of 2-methyl-N-(5-methyl-1,3,4-oxadiazol-2-yl)-3-(methylsulphonyl)-4-(trifluoromethyl)benzamide, (yield 15%).

The invention claimed is:

1. A method for preparing N-(1,3,4-oxadiazol-2-yl)arylcarboxamide of formula (I) by reacting 2-amino-1,3,4-oxadiazoles of formula (II) with benzoic acids of formula (III),

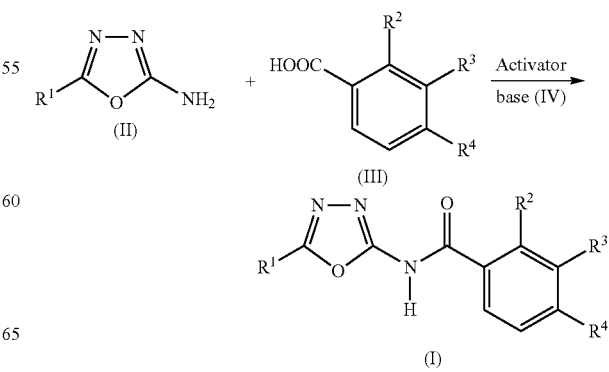

wherein said method is carried out
a) in the presence of an activating reagent selected from the group consisting of thionyl chloride, phosgene, diphosgene, mesyl chloride, tosyl chloride, $POCl_3$, $PCl_5$, oxalyl chloride and $C_1$-$C_8$-alkyl-OC(O)C$_1$, and
(b) in the presence of a base of formula (IV),

(IV)

and
c) where the substituents are as defined herein below:
$R^1$ is hydrogen, $C_3$-$C_{12}$-cycloalkyl, $C_1$-$C_8$-alkyl, $C_1$-$C_5$-alkoxy, halogen, cyano or phenyl,
$R^2$ is hydrogen, $C_1$-$C_5$-alkyl or halogen,
$R^3$ is hydrogen, $C_1$-$C_8$-alkyl, $C_1$-$C_8$-alkylsulphenyl, $C_1$-$C_8$-alkylsulphinyl or $C_1$-$C_8$-alkylsulphonyl,
$R^4$ is $C_1$-$C_5$-alkyl or $C_1$-$C_3$-haloalkyl, and
$R^5$ is $C_1$-$C_{12}$-alkyl or phenyl.

2. The method according to claim 1, wherein the compound of formula (II) is used with an excess of 10% relative to the compound of formula (III).

3. The method according to claim 1, wherein thionyl chloride, phosgene or diphosgene is used as the activating reagent.

4. The method according to claim 1, wherein thionyl chloride is used as the activating reagent.

5. The method according to claim 1, wherein the activating reagent and the compounds of formula (III) are used in a molar ratio of from 1.2 to 1.9.

6. The method according to claim 1, wherein the base of formula (IV) and the compounds of formula (III) are used in a molar ratio of from 1 to 2.5.

7. The method according to claim 1, wherein the method is carried out in the presence of a solvent which is tetrahydrofuran, acetonitrile, 2-methyl-5-ethylpyridine or 3-methylpyridine.

8. The method according to claim 1, wherein the solvent used is 3-methylpyridine.

9. The method according to claim 1, wherein
$R^1$ is hydrogen, methyl, ethyl, n-propyl, isopropyl or phenyl,
$R^2$ is methyl or chlorine,
$R^3$ is methylsulphenyl, methylsulphinyl or methylsulphonyl,
$R^4$ is trifluoromethyl, and
$R^5$ is methyl or n-butyl.

10. The method according to claim 1, wherein
$R^1$ is methyl,
$R^2$ is methyl or chlorine,
$R^3$ is methylsulphonyl,
$R^4$ is trifluoromethyl, and
$R^5$ is methyl.

11. The method according to claim 1, wherein the reaction is conducted in a range of 0° C. to 25° C.

* * * * *